United States Patent [19]
Kebabian

[11] Patent Number: 5,650,845
[45] Date of Patent: Jul. 22, 1997

[54] OPTICAL OXYGEN CONCENTRATION MONITOR

[75] Inventor: Paul Kebabian, Acton, Mass.

[73] Assignee: Aerodyne Research, Billerica, Mass.

[21] Appl. No.: 444,820

[22] Filed: May 18, 1995

[51] Int. Cl.$^6$ .......................... G01N 21/31; G01N 21/35
[52] U.S. Cl. .................... 356/307; 250/339.13; 250/345; 356/437
[58] Field of Search ................................. 356/307, 436, 356/437, 435; 250/339.13, 345

[56] References Cited

U.S. PATENT DOCUMENTS

| | | | |
|---|---|---|---|
| 3,625,621 | 12/1971 | Fields | 356/435 |
| 3,807,876 | 4/1974 | Nakahara et al. | 356/437 |
| 4,035,083 | 7/1977 | Woodriff et al. | 356/307 X |
| 4,341,470 | 7/1982 | Parker et al. | 356/307 |
| 4,815,847 | 3/1989 | Oberheim et al. | 356/307 |
| 5,047,639 | 9/1991 | Wong | 356/436 X |
| 5,198,509 | 3/1993 | Fujiwa et al. | 525/523 |

*Primary Examiner*—Vincent P. McGraw
*Attorney, Agent, or Firm*—Cesari and McKenna, LLP

[57] ABSTRACT

A system for measuring and monitoring the concentration of oxygen uses as a light source an argon discharge lamp, which inherently emits light with a spectral line that is close to one of oxygen's A-band absorption lines. In a preferred embodiment, the argon line is split into sets of components of shorter and longer wavelengths by a magnetic field of approximately 2000 Gauss that is parallel to the light propagation from the lamp. The longer wavelength components are centered on an absorption line of oxygen and thus readily absorbed, and the shorter wavelength components are moved away from that line and minimally absorbed. A polarization modulator alternately selects the set of the longer wavelength, or upshifted, components or the set of the shorter wavelength, or downshifted, components and passes the selected set to an environment of interest. After transmission over a path through that environment, the transmitted optical flux of the argon line varies as a result of the differential absorption. The system then determines the concentration of oxygen in the environment based on the changes in the transmitted optical flux between the two sets of components. In alternative embodiments modulation is achieved by selectively reversing the polarity of the magnetic field or by selectively supplying the magnetic field to either the emitting plasma of the lamp or the environment of interest.

13 Claims, 4 Drawing Sheets

OPTICAL OXYGEN CONCENTRATION MONITOR

This invention was made with government support under Department of Energy Contract No. DE-FG02-93ER81522. The government has certain rights in this invention.

FIELD OF THE INVENTION

This invention relates generally to optical sensors and, more particularly, to sensors for measuring the concentration of oxygen in an environment of interest.

BACKGROUND OF THE INVENTION

Measuring or monitoring the concentration of oxygen is important in areas in which the concentration may fall below safe levels. For example, the concentration of oxygen should be measured and monitored in an industrial plant in which workers are handling asphyxiants such as nitrogen or carbon dioxide, to ensure that the leakage of the asphyxiants into the work area does not cause the oxygen concentration to fall below a safe level. The safe level is typically between the atmospheric concentration of oxygen, which is 21% and a minimum concentration of 19.5%. Otherwise, the workers may be harmed, sometimes fatally, as a result of a lack of oxygen. Similarly, when maintenance workers are entering an enclosed or unventilated space such as a storage tank, sewer, or utility tunnel, it is necessary to measure the concentration of oxygen before entry. Further, it is necessary to monitor the concentration while the workers are inside, to ensure a safe level of oxygen is maintained.

Conversely, measuring the concentration of oxygen in a sealed area can indicate, if the concentration is too high, that a seal is leaking. For example, the sealed space between window panes of a thermally efficient window may be filled with a gas of low thermal conductivity, such as argon. If a relatively high concentration of oxygen is present in the sealed space, it indicates that the argon is escaping and air is entering the space. In this type of application, the concentration of oxygen must be non-invasively measured, to avoid adversely affecting the seal.

Oxygen absorbs light in the 760 nanometer spectral region. Oxygen's absorption spectrum in this region consists of a number of narrow absorption lines that together are referred to as the "atmospheric oxygen A-band." A known prior system for measuring the concentration of oxygen uses a diode laser as a light source, and determines the absorption coefficient of one of the spectral lines of the atmospheric A-band as a function of the laser's wavelength. As long as the laser produces light with a wavelength that is the same as or close to one of the absorption lines of oxygen, the system can determine the concentration of oxygen based on the absorption coefficient of the spectral line.

One of the problems with this type of system is that the diode laser is unreliable. As the laser ages it experiences unpredictable changes in both operating temperature and current required to tune the laser to a given wavelength, which may result in changes in the wavelength or variations in the intensity of the light it produces. To compensate for these changes, the laser system may include a complex feedback mechanism and/or it may require a skilled technician to operate it. This makes the system expensive both to build and to use.

SUMMARY OF THE INVENTION

The invention is an oxygen sensing system that uses as a light source an argon discharge lamp. One of the spectral lines emitted by the neutral argon atom is at a wavelength (in air) of approximately 763.5 nm, close to one of oxygen's A-band absorption lines; the exact wavelengths (in vacuo) are 763.721 nm and 763.729 nm for the argon and oxygen lines, respectively. The oxygen line is designated as P9Q8 in the customary molecular spectroscopic notation for specifying lines within a band. Hereinafter, these lines are referred to as simply the argon line and the oxygen line, since they are the only ones relevant to the operation of the current system.

As an argon lamp ages, the internal operating conditions of the discharge plasma (chiefly, the pressure), gradually change, but the resulting changes in the spectrum of the emitted line, such as its center wavelength and width, are small enough as to have no significant effect other than a gradual drop in the light output. This stands in contrast to the case of a diode laser, where aging can cause abrupt and unpredictable changes in the wavelength of its output.

In its simplest configuration, the system determines the oxygen concentration in the environment of interest based on changes in the optical flux of the argon line, relative to the flux emitted by the lamp, as that light passes through the environment of interest. However, since the argon line and the oxygen line are not at precisely the same wavelength, the absorption coefficient of oxygen is substantially less than if these lines were coincident. Further, this simplest embodiment provides no way to readily distinguish between changes in the optical flux due to the absorption by oxygen and the changes due to other factors, e.g. smoke or dust on the optical elements.

In a preferred embodiment, the light and in particular, the light of the argon line, is split into sets of components of shorter and longer wavelengths by placing the emitting plasma in a magnetic field that is parallel to the direction of the light propagation. This happens as a result of the Zeeman effect, which also results in the upshifted and downshifted components having circular polarizations of opposite handedness. The longer wavelength components are centered on an absorption line of oxygen and the shorter wavelength components are moved away from that line. Accordingly, the longer wavelengths are readily absorbed and the shorter wavelengths are minimally absorbed by the particular oxygen absorption line.

A polarization modulator is used to alternately select left circularly polarized and right circularly polarized light. The polarization modulator thus transmits light that alternately contains wavelengths that are strongly absorbed by the oxygen line and wavelengths that are weakly absorbed. After transmission over a path through an environment in which the concentration of oxygen is to be measured, the optical flux of the argon line varies as a result of the differential absorption. The system then determines the concentration of oxygen in the environment based on the variation in the detected optical flux between the transmission of the weakly absorbed components and the transmission of the strongly absorbed components.

The polarization modulator consists of (i) a quarter-wave plate that converts the circular polarizations of the upshifted and downshifted sets of components to linear polarizations; (ii) a liquid crystal cell that, based on its state, rotates or refrains from rotating the polarizations of the upshifted and downshifted components; and (iii) a linear polarizer that passes components of a particular polarization and blocks components of the orthogonal polarization. When the liquid crystal cell is de-energized, it rotates the linear polarized components 90 degrees. Since the upshifted and downshifted components have perpendicular linear polarizations when they enter the cell, after having passed through the quarter-wave plate, the cell rotates them such that the linear polarizer passes the set of components that, without the rotation, it blocked. The cell is periodically energized and de-energized, such that upshifted and downshifted components of the light are alternately passed by the linear polarizer to the environment in which oxygen is to be measured.

Before the light travels through the environment of interest, it passes through an optical tap, which extracts a portion of the light and transmits it to a first photodiode. This photodiode produces an output signal that is proportional to the optical flux of the argon line in the extracted light. The remainder of the light is transmitted through the environment of interest to a second photodiode, which also produces an output signal that is proportional to the optical flux of the argon line. The system then determines the concentration of oxygen in the environment of interest from the output signals of the two photodiodes during the two modes of operation, i.e., the mode in which weakly absorbed components are transmitted and the mode in which strongly absorbed components are transmitted. The first photodiode is included to allow the system to compensate for differential amplitude modulation between the two modes of operation that may result in a difference in the optical flux of the argon line in the light transmitted to the environment of interest, as well as for random changes that may occur in the lamp output.

In an alternative embodiment, modulation is achieved by alternately reversing the polarity of the magnetic field, to reverse the circular polarizations of the sets of components, and passing the sets of components through a fixed circular polarizer. The polarizer passes the set of components with, for example, right-handed circular polarization and blocks the set of components with left-handed circular polarization. Accordingly, the system selects which set of components is passed through the circular polarizer to the environment of interest by alternating the polarity of the magnetic field.

In another alternative embodiment, modulation is achieved by alternately supplying and removing the magnetic field. When the magnetic field is present, the light is split into the sets of upshifted and downshifted components, as discussed above. When these sets of components are passed through the environment of interest, the upshifted components are readily absorbed and the downshifted components are minimally absorbed. When the magnetic field is absent, the light produced by the lamp is passed directly to the environment of interest. Since this light has a wavelength that is close to but not the same as the oxygen line, the oxygen does not as readily absorb this light. The differences in absorption between the shifted components and the unshifted light are then used to determine the concentration of oxygen.

In this alternative embodiment, the inclusion of a circular polarizer to select the upshifted components is optional. The advantage of including the circular polarizer is that, by excluding the downshifted components, the contrast in absorption between field-on and field-off states is maximized. The advantage of omitting the circular polarizer is that the attendant optical losses attributable to the polarizer are avoided. In most practical systems, it will be preferable to include the circular polarizer.

Modulation may also be achieved by selectively applying the magnetic field to the environment of interest so as to periodically shift the oxygen line to bring one of the split components coincident with the unshifted by the selective application of the magnetic field, as discussed wavelength of light emitted by the lamp. The spectral output of the lamp is left constant, and the oxygen spectral lines are alternately shifted and unshifted by the selective application of the magnetic field, as discussed below.

BRIEF DESCRIPTION OF THE DRAWINGS

The above and further advantages of the invention may be better understood by referring to the following description in conjunction with the accompanying drawings, in which.

DETAILED DESCRIPTION OF ILLUSTRATIVE EMBODIMENTS

Figure 1:
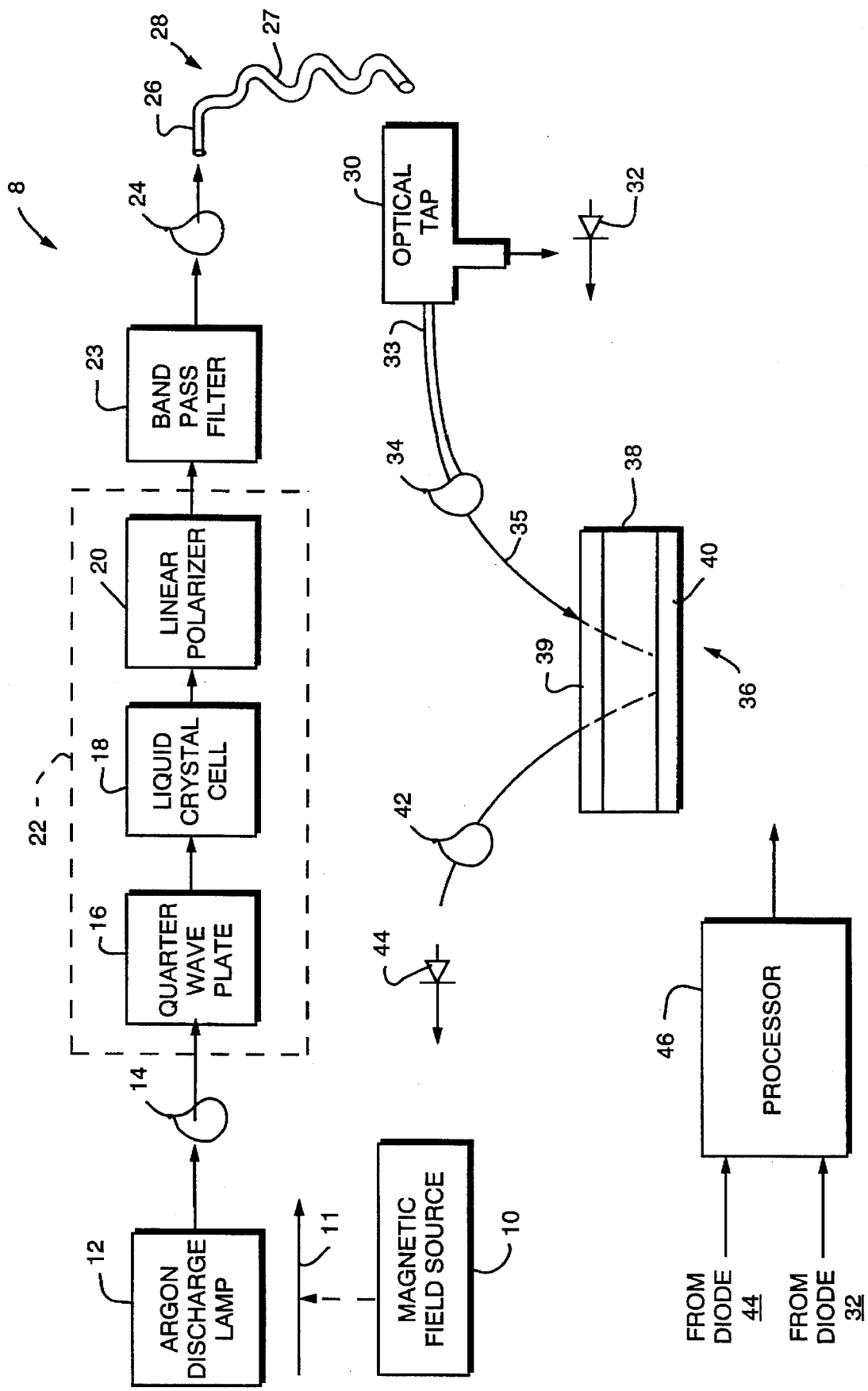
FIG. 1 is a functional block diagram of a system constructed in accordance with a preferred embodiment.

FIG. 1 depicts a system 8 that non-invasively measures the oxygen concentration in an environment of interest, i.e., a sample or cell 36, which is depicted in the drawing as the sealed space between the panes 39 and 40 of a window 38. An argon discharge lamp 12, operating in a conventional manner, supplies light at a wavelength of approximately 763.5 nanometers, which is close to an oxygen absorption line in the atmospheric A-band. A magnetic field source 10 supplies to the emitting plasma of the lamp a magnetic field that is parallel to the light propagation from the lamp 12, as depicted by the arrow 11.

The magnetic field, in accordance with the well known Zeeman effect, splits the light into upshifted and downshifted sets of components of, respectively, longer and shorter wavelengths. These sets are circularly polarized in opposite directions. With a magnetic field strength of approximately 2000 Gauss, the longer wavelengths are centered on a particular oxygen absorption line and the shorter wavelengths are moved away from the line.

A lens 14 collimates the light and a quarter-wave plate 16 converts the circular polarizations to linear polarizations. The light then passes to a liquid crystal cell 18, which is in one of two states, namely, energized or de-energized. When the cell is de-energized, it rotates the collimated light by 90 degrees, and thus, reverses the polarizations of the sets of components. When the cell is in its energized state, it does not rotate the polarization.

A linear polarizer 20 receives the light transmitted through the cell 18, and passes the set of components with a particular polarization and blocks the set with the orthogonal polarization. It thus passes, for example, the set of upshifted components transmitted to it when the liquid crystal cell 18 is de-energized, and passes the set of downshifted components transmitted to it when the cell is energized. The linear polarizer thus alternately passes the set of components that is readily absorbed by the oxygen and the set of components that is minimally absorbed. The quarter-wave plate 16, liquid crystal cell 18 and linear polarizer 20 together form a polarization modulator 22. As necessary, a bandpass filter 23 is included to filter from the modulated light unwanted, or extraneous, components, that is, the other spectral lines emitted by the argon lamp.

A lens 24 focuses the light into an optical fiber 26. A mode scrambler 28, which is a length of fiber with strategically placed bends 27, randomizes the angles of the individual light rays with respect to the fiber axis. The scrambler 28 thus produces light that is more uniform both spatially and with respect to the range of directions of propagation of the light rays through the fiber. This ensures that an optical tap 30 is able to direct a constant fraction of the light to a photodiode 32, regardless of small fluctuations in the angular or spatial distribution of the light emitted by the lamp. In response, the photodiode 32 produces a signal that is proportional to the intensity of the beam passed by the filter 23.

The optical tap 30 passes the remainder of the light over a fiber 33, through a focusing lens 34 and over a path through the environment of interest 36. This environment is depicted in the drawing as the sealed space between the panes 39 and 40 of a window 38.

Figure 2:
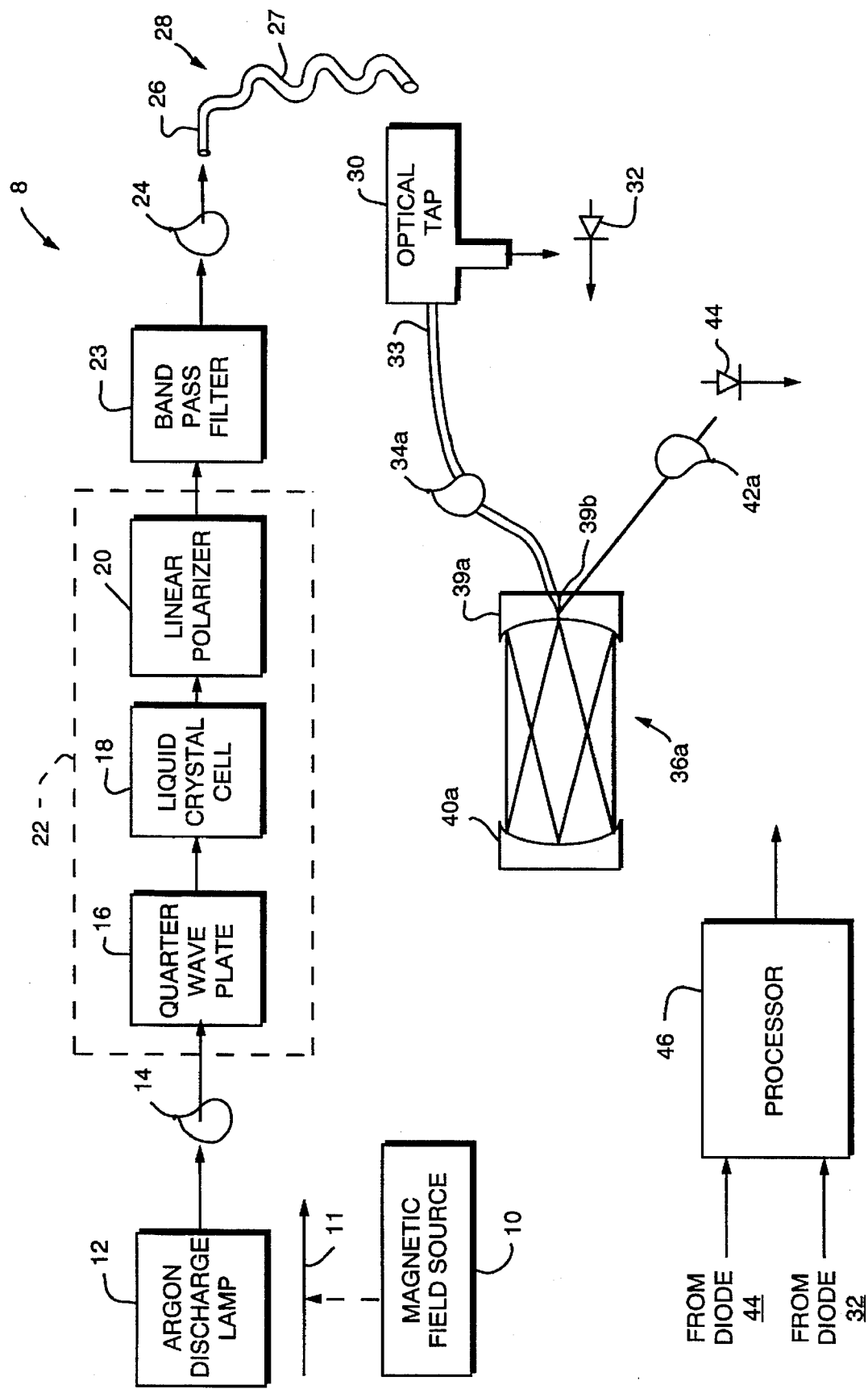
FIG. 2 is the system of FIG. 1 including as an environment of interest a multi-pass absorption cell.

When the environment of interest is not sealed but rather is open, such as a tunnel or a room, a sample of air from the area may be allowed to diffuse into a multiple pass absorption cell 36a, as depicted in FIG. 2. The benefit of a multiple pass over a single pass arrangement, such as the arrangement 36 depicted in FIG. 1, is that the multiple pass cell provides a longer path, and thus, a larger absorption signal, for a given overall size.

Referring now to FIG. 2, the light from optical tap 30 is coupled through a lens 34a into the cell 36a through a hole 39b in a mirror 39a. The mirror 39a and an opposing mirror 40a reflect the light in multiple passes between them. The last pass of the light from mirror 40a directs the light from the cell through the hole 39b to a lens 42a. In an alternative configuration, the air sample may be drawn into the cell 36a by a small pump or fan (not shown).

Referring again to FIG. 1, the light transmitted to the window 38 reflects off the rear pane 40, and passes through a focusing lens 42 to a second photodiode 44. This photodiode produces a signal that is proportional to the intensity of the reflected light. A processor 46 determines the concentration of oxygen in the sealed window 38 based on the differences in the output signals of the photodiodes between the two modes of operation, i.e., between the transmission of the weakly absorbed components and the transmission of the strongly absorbed components. If the concentration exceeds a predetermined threshold, the processor 46 determines that the seal is leaking.

In the preferred embodiment the two photodiodes are part of a bridge circuit (not shown). The bridge is electrically balanced to compensate for changes in the photodiode output signals that are attributable to the operating characteristics of the system components. The liquid crystal cell 18, for example, may introduce amplitude modulation into the signal transmitted to the environment of interest. Changes in the output of the bridge in response to the two modes of operation are then attributable to the differential absorption of the light by the oxygen that is present within that environment.

The processor 46 may determine, instead of the actual concentration of oxygen, whether or not the concentration exceeds or falls below a predetermined level. It thus determines, for example, if the signal produced by the bridge circuit in response to the upshifted components being passed through the environment is above or below a predetermined threshold value. If the system is determining the oxygen concentration in an inhabited area, the threshold represents a safe level of oxygen. If the system is determining if a seal is leaking, the threshold represents a level that indicates that air is replacing the gas in the sealed environment.

Figure 3:
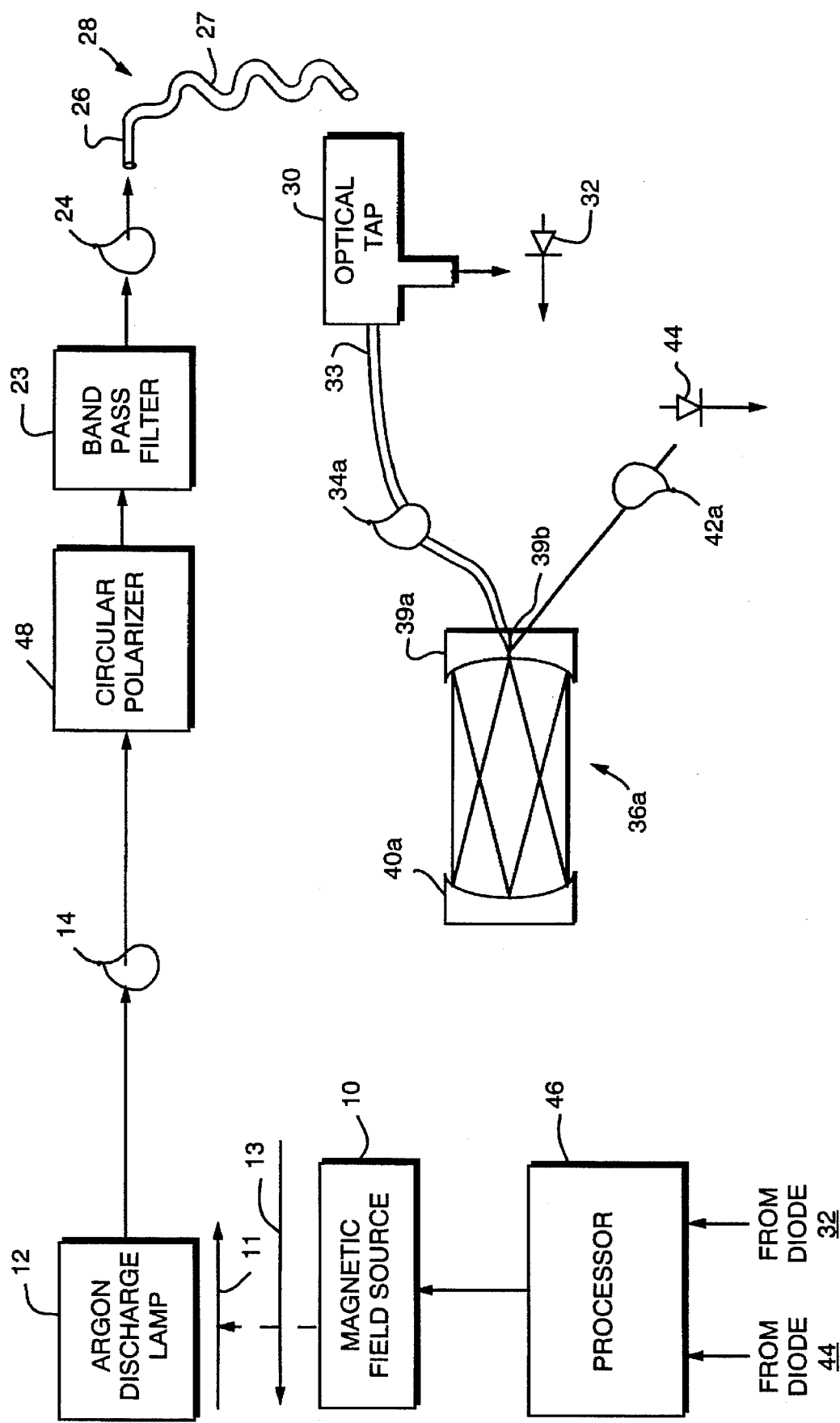
FIG. 3 is a functional block diagram of a system constructed in accordance with an alternative embodiment in which a polarization modulator of FIG. 2 is replaced by a fixed circular polarizer.

In an alternative embodiment depicted in FIG. 3, modulation is achieved by reversing the polarity of the magnetic field produced by the magnetic field source 10. The magnetic field source, under the control of the processor 46, alternately supplies a magnetic field that is oriented in the same direction as the light propagates from the lamp and a magnetic field that is oriented in the opposite direction, as indicated, respectively, by arrows 11 and 13. The change in the polarity of the magnetic field results in a reversal of the circular polarizations of the upshifted and downshifted components. A fixed circular polarizer 48 passes one set of these components to the optical fiber 26 and blocks the other set. The particular set passed by the polarizer depends on the polarizations, and thus, on the polarity of the magnetic field. In this embodiment, the polarization modulator 22 (FIG. 1) is eliminated.

In a second alternative embodiment, the magnetic field source 10 is alternately turned on and off, to provide the modulation. The fixed circular polarizer 48 is thus no longer required. When the magnetic field source is turned on, a magnetic field is present and the light from the argon discharge lamp 12 is split into the sets of upshifted and downshifted components, as discussed above. The set of upshifted components are readily absorbed by the oxygen line and the downshifted components are minimally absorbed by that line. When the magnetic field source is turned off, the wavelength of the light produced by the lamp is close to the wavelength of the oxygen line and absorption occurs, but not as readily as with the set of upshifted components. The differences in absorption in the presence and absence of the magnetic field can then be used to determine the concentration of oxygen, as discussed above.

Figure 4:
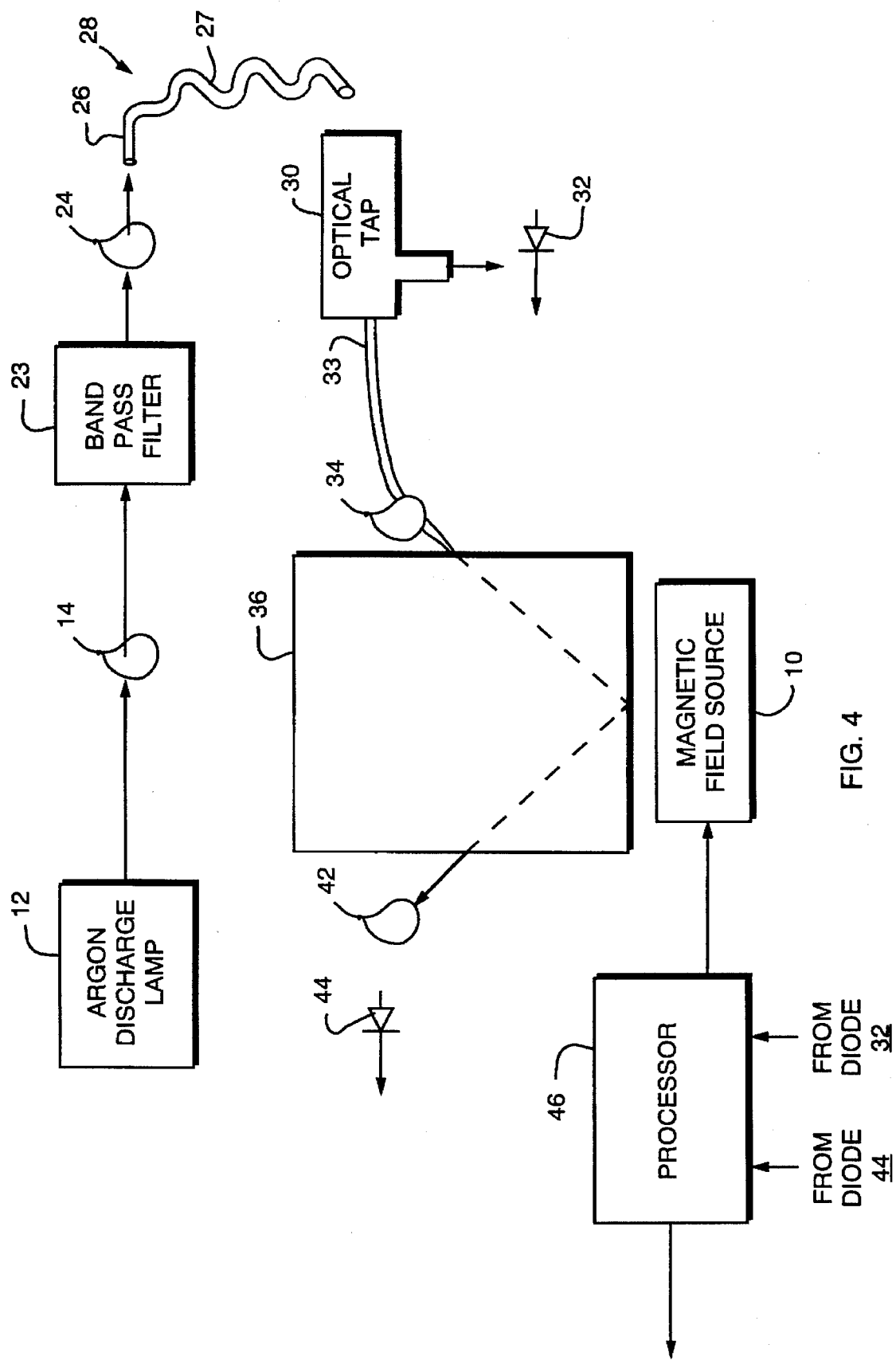
FIG. 4 is a functional block diagram of another alternative embodiment.

In another embodiment, which is depicted in FIG. 4, the magnetic field source 10 is moved to the cell 36, to produce a magnetic field therein. Oxygen's absorption lines exhibit the Zeeman effect. Accordingly, in the presence of a magnetic field of appropriate strength the oxygen line can be split into upshifted and downshifted components such that one of the components coincides with the wavelength of light produced by the argon discharge lamp 12. Modulation is achieved by cycling the magnetic field on and off.

There are essentially two types of argon discharge lamps available commercially, namely, positive column lamps and surface glow lamps. Either type of lamp may be used in the system discussed above, however, the surface glow lamp is preferred. The surface glow lamp requires a lower operating voltage and tends to produce a steadier intensity of light in the presence of a magnetic field. Further, since the plasma in a surface glow lamp is confined to a fraction of a millimeter above the lamp's cathode, a relatively small magnet may be used to produce the magnetic field. Finally, the surface glow lamps are less expensive than the positive column lamps.

The system in any of its embodiments is less complex than the prior systems that use laser diodes as the light sources. Further, the current system is easier to operate, since the aging of the system and/or its operating conditions have no appreciable effect on the wavelength of the light produced by the lamp.

The foregoing description has been limited to specific embodiments of this invention. It will be apparent, however, that variations and modifications may be made to the invention, with the attainment of some or all of its advantages. Therefore, it is the object of the appended claims to cover all such variations and modifications as come within the true spirit and scope of the invention.

What is claimed is:

1. A system for determining the concentration of oxygen in an environment of interest, the system including:
   A. an argon discharge lamp for selectively supplying to the environment of interest light in a spectral line having a wavelength of approximately 763.5 nm, which is close to a spectral absorption line of oxygen; and
   B. means for determining the concentration of oxygen in the environment of interest based on variations in optical flux in the light supplied by the lamp to the environment of interest.

2. The system of claim 1 further including:
   A. a magnetic field source for supplying a magnetic field that splits the light supplied by the lamp into a set of upshifted components with wavelengths that are readily absorbed by the oxygen line and a set of downshifted components with wavelengths that not as readily absorbed by the oxygen line;
   B. a polarization modulator for selectively passing to the environment of interest the upshifted components or the downshifted components; and
   C. the means for determining the concentration of oxygen in the environment of interest determines the concentration based on variations in the transmitted optical flux of the light when the set of upshifted components is supplied to the environment of interest.

3. The system of claim 2, wherein the means for determining the concentration of oxygen includes:
   i. a first photodiode for producing a signal that is proportional to the transmitted optical flux of the set of upshifted components that has not passed through the environment of interest;
   ii. a second photodiode for producing a signal that is proportional to the transmitted optical flux of the set of upshifted components that has passed through the environment of interest; and
   iii. means for determining, from the differences in the signals produced by the first and the second photodiodes, the concentration of oxygen in the environment of interest.

4. The system of claim 3, wherein:
   iv. the first photodiode produces a signal that is proportional to the transmitted optical flux of the set of downshifted components that has not passed through the environment of interest;
   v. the second photodiode produces a signal that is proportional to the transmitted optical flux of the set of downshifted components that has passed through the environment of interest; and
   vi. the means for determining, based on the differences in the signals produced by the first and the second photodiodes in response to the set of downshifted components, determines corrections to be included in determining the concentration of oxygen based on the signals associated with the set of upshifted components.

5. The system of claim 4, wherein the means for determining the concentration of oxygen includes a bridge that includes the two photodiodes, the means electrically balancing the bridge when the set of downshifted components are passed to the environment of interest, the means further producing a signal that is proportional to the concentration of oxygen in the environment of interest when the set of upshifted components are passed to the environment of interest.

6. The system of claim 5, wherein the means for determining the concentration of oxygen determines if the concentration exceeds or falls below a predetermined level by determining if the output signal produced by the bridge exceeds or falls below a predetermined value.

7. The system of claim 2, wherein the means for determining the concentration of oxygen determines if the concentration exceeds or falls below a predetermined level.

8. The system of claim 2, wherein the polarization modulator includes:
   i. means for linearizing a circular polarization of the upshifted and downshifted components;
   ii. rotating means for selectively rotating the components, the rotating means operating in a first mode in which it refrains from rotating the components and in a second mode in which it rotates the components such that the upshifted components and downshifted components, respectively, have polarizations that are the opposite of the polarizations they had when the rotating means is operating in the first mode; and
   iii. a linear polarizer for passing the components having a particular polarization and refraining from passing the components that do not have the particular polarization.

9. The system of claim 2 wherein the polarization modulator includes:
   i. means for controlling the magnetic field source, such that the magnetic field source selectively reverses the polarity of the magnetic field and produces upshifted and downshifted components of reversed circular polarizations; and
   ii. a circular polarizer, for passing components of a particular circular polarization and refraining from passing components that do not have the particular circular polarization.

10. The system of claim 2 wherein the polarization modulator includes means for selectively turning on and off the magnetic field source, such that the light produced by the lamp is selectively split into the sets of upshifted and downshifted components and not split into the sets of components, the polarization modulator alternately passing to the environment of interest the split components and the unsplit components.

11. A system for determining the concentration of oxygen in an environment of interest, the system including:
   A. an argon discharge lamp for supplying light to the environment of interest;
   B. a magnetic field source for supplying a magnetic field that splits the light supplied by the lamp into a set of upshifted components with wavelengths that are readily absorbed by an oxygen absorption spectral line and a set of downshifted components with wavelengths that are not as readily absorbed by the oxygen absorption line;
   C. control means for selectively controlling the magnetic field source to provide a magnetic field of one polarity or a reverse polarity, the polarity of the magnetic field determining the circular polarizations of the sets of upshifted and downshifted components;
   D. a circular polarizer for selectively passing to the environment of interest the set of upshifted components or the set the downshifted components, depending on the orientations of the circular polarizations; and
   E. means for determining the concentration of oxygen in the environment of interest based on variations in the transmitted optical flux of the argon line when the set of upshifted components is supplied to the environment of interest.

12. A system for determining the concentration of oxygen in an environment of interest, the system including:

A. an argon discharge lamp for supplying light to the environment of interest;

B. a magnetic field source for supply a magnetic field that splits the light supplied by the lamp into a set of upshifted components with wavelengths that are readily absorbed by an oxygen absorption spectral line and a set of downshifted components with wavelengths that not as readily absorbed by the oxygen absorption line;

C. control means for selectively turning on the magnetic field source and turning off the magnetic field source;

D. means for determining the concentration of oxygen in the environment of interest based on variations in the transmitted optical flux of the argon line between (i) the sets of upshifted and downshifted components being supplied to the environment of interest when the magnetic field source is turned on, and (ii) unshifted light being supplied to the environment of interest when the magnetic field source is turned off.

13. A system for determining the concentration of oxygen in an environment of interest, the system including:

A. an argon discharge lamp for supplying light to the environment of interest;

B. a magnetic field source for supplying a magnetic field to the environment of interest, the magnetic field splitting an oxygen spectral line into a set of downshifted components with wavelengths that readily absorb a spectral line in the light produced by the argon lamp and a set of upshifted components with wavelengths that do not as readily absorb the spectral line;

C. control means for selectively turning on the magnetic field source and turning off the magnetic field source;

D. means for determining the concentration of oxygen in the environment of interest based on variations in the transmitted optical flux of the light between times when (i) the magnetic field source is turned on and sets of upshifted and downshifted components are present in the environment of interest, and (ii) the magnetic field source is turned off and unshifted components are present in the environment of interest.

* * * * *